(12) United States Patent
Ternes

(10) Patent No.: US 8,676,307 B2
(45) Date of Patent: *Mar. 18, 2014

(54) ELECTRICAL ENERGY DELIVERY TISSUE SITE VALIDATION

(75) Inventor: David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 179 days.

This patent is subject to a terminal disclaimer.

(21) Appl. No.: 13/237,491

(22) Filed: Sep. 20, 2011

(65) Prior Publication Data

US 2012/0010675 A1 Jan. 12, 2012

Related U.S. Application Data

(63) Continuation of application No. 11/549,439, filed on Oct. 13, 2006, now Pat. No. 8,036,739.

(51) Int. Cl.
*A61N 1/00* (2006.01)

(52) U.S. Cl.
USPC .......................................................... 607/2

(58) Field of Classification Search
None
See application file for complete search history.

(56) References Cited

U.S. PATENT DOCUMENTS

| 5,405,365 | A | 4/1995 | Hoegnelid et al. |
| 7,020,530 | B1 | 3/2006 | Ideker et al. |
| 8,036,739 | B2 | 10/2011 | Ternes |
| 2002/0087089 | A1 | 7/2002 | Ben-Haim |
| 2004/0172075 | A1 | 9/2004 | Shafer et al. |
| 2006/0095081 | A1 | 5/2006 | Zhou et al. |
| 2007/0282385 | A1 | 12/2007 | Rossing et al. |
| 2008/0091243 | A1 | 4/2008 | Ternes |

FOREIGN PATENT DOCUMENTS

| EP | 1078649 A1 | 2/2001 |
| EP | 2086633 B1 | 7/2012 |
| JP | 3004877 A | 1/1991 |
| JP | 2004194936 A | 7/2004 |
| WO | WO-02096512 A1 | 12/2002 |
| WO | WO-2006049539 A1 | 5/2006 |
| WO | WO-2008048440 A1 | 4/2008 |

OTHER PUBLICATIONS

U.S. Appl. No. 11/549,439, Final Office Action mailed Jul. 1, 2010, 12 pgs.
U.S. Appl. No. 11/549,439, Non Final Office Action mailed Dec. 23, 2010, 11 pgs.
U.S. Appl. No. 11/549,439, Non-Final Office Action mailed Oct. 19, 2009, 10 pgs.

(Continued)

*Primary Examiner* — Eric D. Bertram
*Assistant Examiner* — Elizabeth K So
(74) *Attorney, Agent, or Firm* — Schwegman Lundberg & Woessner, P. A.

(57) ABSTRACT

Electrical energy delivery tissue site validation systems and methods can determine an indication of a tissue type at a tissue site. This information can be used to enable or inhibit electrical energy delivery to the tissue site. The tissue type at the tissue site can be determined such as by delivering a test electrical energy and sensing a responsive electrical energy. An electrical connectivity to the tissue site can also be determined, such as by using a sensed intrinsic electrical signal at the tissue site. Tissue type information may be communicated externally, such as to allow user confirmation or override of the determined indication of tissue type at the tissue site, such as by a physician, user, or other operator.

20 Claims, 9 Drawing Sheets

(56) References Cited

OTHER PUBLICATIONS

U.S. Appl. No. 11/549,439, Notice of Allowance mailed Jun. 14, 2011, 5 pgs.
U.S. Appl. No. 11/549,439, Response filed Mar. 23, 2011 to Non Final Office Action mailed Dec. 23, 2010, 15 pgs.
U.S. Appl. No. 11/549,439, Response filed Apr. 19, 2010 to Non Final Office Action mailed Oct. 19, 2009, 26 pgs.
U.S. Appl. No. 11/549,439, Response filed Aug. 10, 2009 to Restriction Requirement mailed Jul. 8, 2009, 8 pgs.
U.S. Appl. No. 11/549,439, Response filed Nov. 1, 2010 to Final Office Action mailed Jul. 1, 2010, 12 pgs.
U.S. Appl. No. 11/549,439, Restriction Requirement mailed Jul. 8, 2009, 6 pgs.
European Application Serial No. 07839393.1, Office Action mailed Oct. 2, 2009, 2 pgs.
PCT Application Serial No. PCT/US2007/021577, International Search Report mailed Mar. 6, 2008, 4 pgs.
PCT Application Serial No. PCT/US2007/021577, Written Opinion mailed Mar. 6, 2008, 7 pgs.
European Application Serial No. 07839393.1, Response filed Feb. 10, 2010 to Office Action mailed Oct. 2, 2009, 12 pgs.
Japanese Application Serial No. 2009-532378, Response filed Sep. 3, 2012 to Office Action mailed Jun. 5, 2012, (w/ English Translation of Amended Claims), 6 pgs.
PCT Application Serial No. PCT/US2007/021577, International Preliminary Report on Patentability Apr. 23, 2009, 8 pgs.
Japanese Application Serial No. 2009-532378, Non Final Office Action dated Jun. 5, 2012, English Translation, 7.

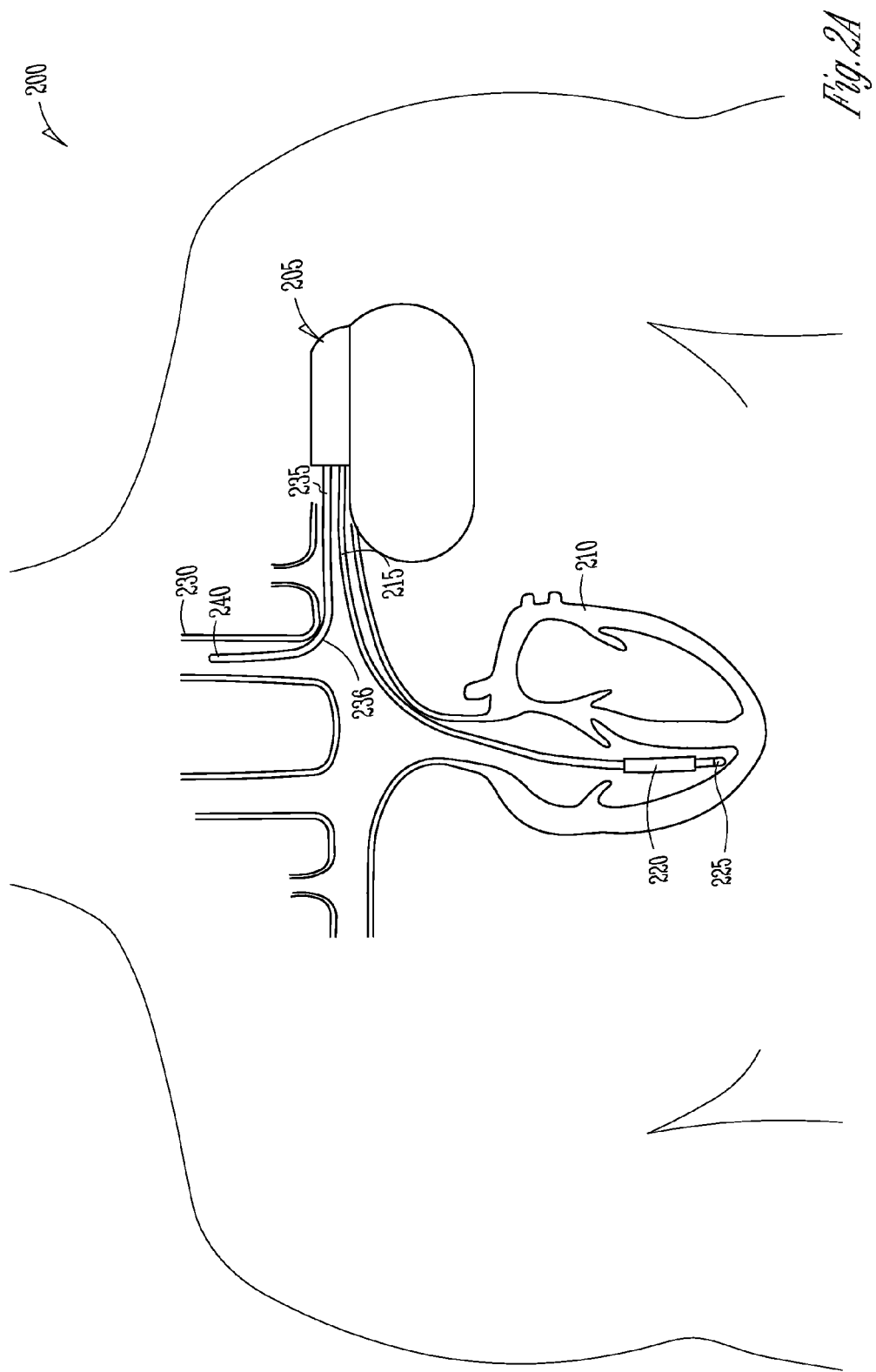

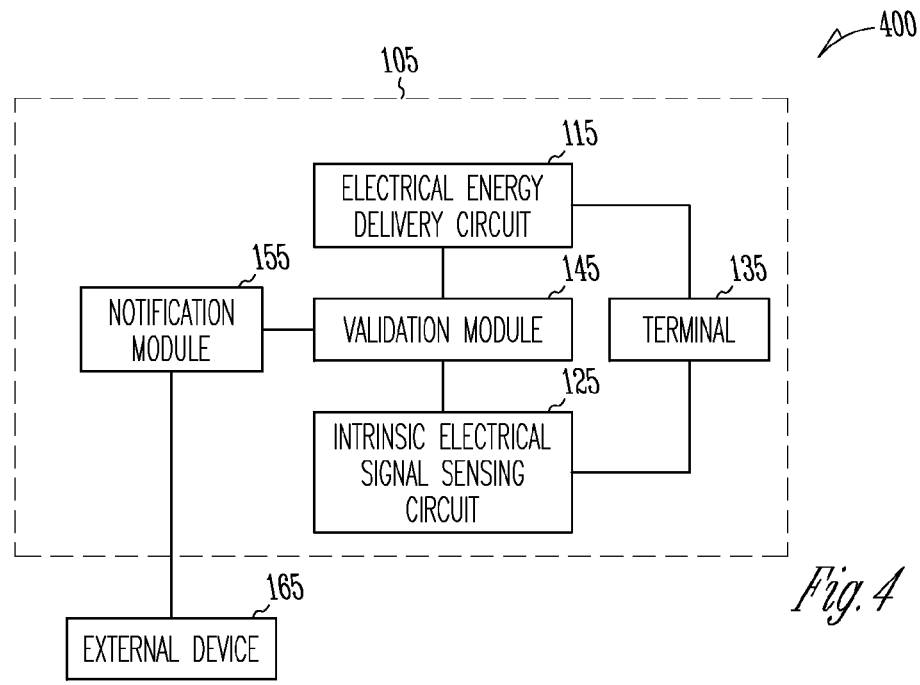
Fig. 3
Fig. 4
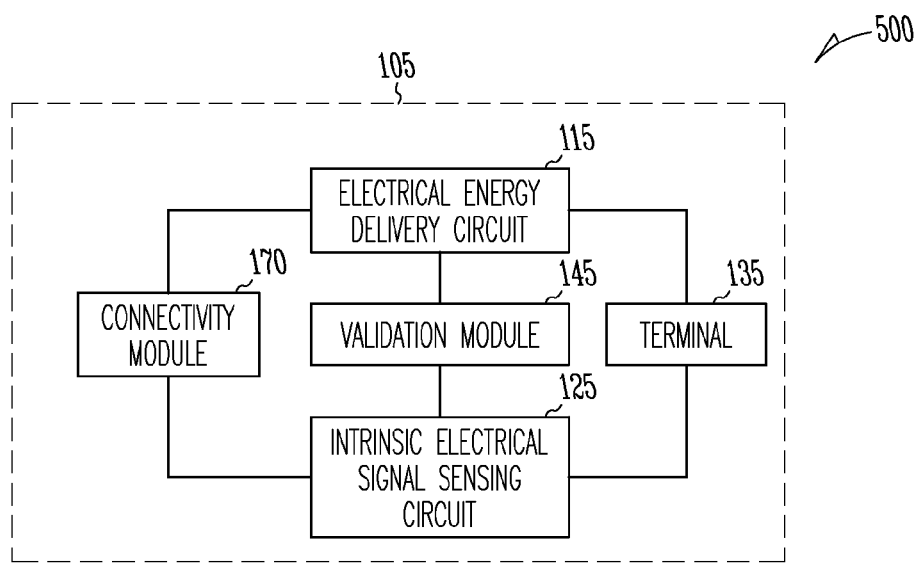
Fig. 5

ELECTRICAL ENERGY DELIVERY TISSUE SITE VALIDATION

CLAIM OF PRIORITY

This application is a continuation of and claims the benefit of priority under 35 U.S.C. §120 to David Ternes, U.S. patent application Ser. No. 11/549,439, entitled "Electrical Energy Delivery Tissue Site Validation," filed on Oct. 13, 2006, now issued as U.S. Pat. No. 8,036,739, which is hereby incorporated by reference herein in its entirety.

TECHNICAL FIELD

This patent document pertains generally to implantable medical devices, and more particularly, but not by way of limitation, to electrical energy delivery tissue site validation.

BACKGROUND

Certain patients exhibit a need for cardiac or neural stimulation, such as by using an implantable medical device. When such a need exists, cardiac tissue can receive cardiac electrostimulation. Such stimulation can evoke a resulting heart contraction, and can be used to maintain a rate of heart contractions that will meet a patient's metabolic need for cardiac output, or to spatially coordinate heart contractions such as to improve the heart's pumping efficiency. Similarly, non-cardiac neural tissue can receive neural stimulation, e.g., neurostimulation energy. Neurostimulation may be used to affect the autonomic balance between the sympathetic nervous system (which tends to speed up certain metabolic processes) and the parasympathetic nervous system (which tends to slow down certain metabolic processes). Some patients may benefit from both cardiac and neural stimulation.

OVERVIEW

The present inventors have recognized that, among other things, it may be undesirable to deliver electrical energy to tissue that was not meant to receive the delivered electrical energy. For example, delivery of a cardiac pacing or shocking energy to a non-cardiac tissue, such as a nerve, might damage or otherwise impair the non-cardiac tissue. Even if delivery of a cardiac pacing or shocking energy to a non-cardiac tissue, such as a vein wall, does not cause damage, it might not provide the intended benefit of the cardiac pacing or shocking energy. In a similar vein, delivery of a neural stimulation energy to a cardiac tissue might damage or otherwise impair the cardiac tissue, or may induce pro-arrhythmic conditions. Thus, the present inventors have recognized, among other things, an unmet need for automatic electrical energy delivery tissue site validation for implantable medical devices.

In certain examples, electrical energy delivery tissue site validation systems and methods can determine an indication of a tissue type at a tissue site. This information can be used to enable or inhibit electrical energy delivery to the tissue site. The tissue type at the tissue site can be determined such as by delivering a test electrical energy and sensing a responsive electrical energy. An electrical connectivity to the tissue site can also be determined, such as by using a sensed intrinsic electrical signal at the tissue site. Tissue type information may be communicated externally, such as to allow user confirmation or override of the determined indication of tissue type at the tissue site, such as by a physician, user, or other operator.

In Example 1, a system includes an implantable medical device. The implantable medical device includes an electrical energy delivery circuit. The implantable medical device also includes an intrinsic electrical signal sensing circuit. The implantable medical device also includes at least one terminal, configured to couple the electrical energy delivery circuit and the intrinsic electrical signal sensing circuit to at least one tissue site. The implantable medical device also includes a validation module, coupled to the electrical energy delivery circuit and the intrinsic electrical signal sensing circuit, wherein the validation module is configured to determine at least one indication of a tissue type at the at least one tissue site using an intrinsic electrical signal received from the intrinsic electrical signal sensing circuit, wherein the validation module is configured to automatically enable or inhibit electrical energy delivery by the electrical energy delivery circuit to the at least one tissue site using the at least one indication of the tissue type.

In Example 2, the intrinsic electrical signal sensing circuit of Example 1 is optionally configured to sense at least one intrinsic cardiac signal.

In Example 3, the intrinsic electrical signal sensing circuit of Examples 1-2 is optionally configured to sense at least one intrinsic neural signal.

In Example 4, the validation module of Examples 1-3 is optionally configured to distinguish between a cardiac tissue site and a neural tissue site.

In Example 5, the system of Examples 1-4 optionally includes at least one lead, configured to couple the at least one terminal to the at least one tissue site, wherein the at least one lead comprises at least one electrode.

In Example 6, the at least one lead of Examples 1-5 optionally includes multiple electrodes, wherein at least one electrode is configured to contact a cardiac tissue site to provide a pacing energy, and wherein at least one electrode is configured to contact a neural tissue site to provide a neurostimulation energy.

In Example 7, the validation module of Examples 1-6 is optionally configured to automatically enable or inhibit electrical energy delivery at multiple tissue sites.

In Example 8, the validation module of Examples 1-7 optionally includes a user confirmation or override, wherein the user confirmation or override is configured to confirm or override the validation module prior to automatically enabling or inhibiting the delivery of electrical energy.

In Example 9, the electrical energy delivery circuit of Examples 1-8 is optionally configured to deliver a pacing energy.

In Example 10, the electrical energy delivery circuit of Examples 1-9 is optionally configured to deliver a neurostimulation energy.

In Example 11, the system of Examples 1-10 optionally includes notification module, coupled to the validation module, wherein the notification module is configured to communicate information of the tissue type at the tissue site to an external device.

In Example 12, the electrical energy delivery circuit of Examples 1-11 is optionally configured to deliver a test electrical energy to the at least one tissue site, wherein the intrinsic electrical signal sensing circuit is configured to detect an intrinsic response energy in response to the test electrical energy, and wherein the validation module is configured to determine at least one indication of a tissue type at the at least one tissue site the intrinsic response energy.

In Example 13, the test electrical energy of Example 1-12 optionally includes a pacing energy.

In Example 14, the test electrical energy of Examples 1-13 optionally includes a neurostimulation energy.

In Example 15, the test electrical energy of Examples 1-14 optionally includes a test electrical energy that is safe for neural tissue and sufficient to trigger a cardiac response.

In Example 16, the system of Examples 1-15 optionally includes a connectivity module, coupled to the electrical energy delivery circuit and the intrinsic electrical signal sensing circuit, wherein the connectivity module is configured to detect an electrical connectivity to the at least one tissue site, and wherein the connectivity module is configured to automatically enable or inhibit electrical energy delivery by the electrical energy delivery circuit to the at least one tissue site using the detected electrical connectivity to the at least one tissue site.

In Example 17, a system includes means for sensing at least one intrinsic electrical signal at a corresponding at least one tissue site, such as by using at least one terminal to couple the system to the at least one tissue site. The system also includes means for determining at least one indication of a tissue type at the at least one tissue site using the at least one intrinsic electrical signal, such as by using a validation module to determine at least one indication of a tissue type at the at least one tissue site using the at least one intrinsic electrical signal sensed at the corresponding at least one tissue site. The system also includes means for automatically enabling or inhibiting electrical energy delivery to the at least one tissue site using the at least one indication of the tissue type, such as by using the validation module to automatically enable or inhibit electrical energy delivery by an electrical energy delivery circuit to the at least one tissue site using the at least one indication of the tissue type at the at least one tissue site.

In Example 18, a method includes sensing at least one intrinsic electrical signal at a corresponding at least one tissue site. The method also includes determining at least one indication of a tissue type at the at least one tissue site using the at least one intrinsic electrical signal. The method also includes automatically enabling or inhibiting electrical energy delivery to the at least one tissue site using the at least one indication of the tissue type.

In Example 19, the sensing of Example 18 optionally includes sensing an intrinsic cardiac signal.

In Example 20, the sensing of Examples 18-19 optionally includes sensing an intrinsic neural signal that is different from an intrinsic cardiac signal.

In Example 21, the sensing at least one intrinsic electrical signal of Examples 18-20 optionally includes using at least one electrode to sense at least one intrinsic cardiac signal and at least one electrode to sense at least one intrinsic neural signal, wherein the multiple electrodes are coupled to a single lead.

In Example 22, the automatically enabling or inhibiting electrical energy delivery of Examples 18-21 optionally includes automatically enabling or inhibiting at multiple tissue sites.

In Example 23, the automatically enabling or inhibiting of Examples 18-22 optionally includes obtaining user confirmation or override before the enabling or inhibiting.

In Example 24, the delivering an electrical energy of Examples 18-23 optionally includes delivering a pacing energy.

In Example 25, the delivering an electrical energy of Examples 18-24 optionally includes delivering a neurostimulation energy.

In Example 26, the determining at least one indication of a tissue type at the at least one tissue site of Examples 18-25 optionally includes delivering a test electrical energy to the at least one tissue site and detecting a test electrical signal response to the delivering of the test electrical energy to the at least one tissue site.

In Example 27, the delivering a test electrical energy of Examples 18-26 optionally includes delivering a pacing energy.

In Example 28, the delivering a test electrical energy of Examples 18-27 optionally includes delivering a neurostimulation energy.

In Example 29, the method of Examples 18-28 optionally includes communicating to an external device information about the tissue type at the tissue site.

In Example 30, the method of Examples 18-29 optionally include determining an electrical connectivity to the at least one tissue site and automatically enabling or inhibiting electrical energy delivery to the at least one tissue site using the determined electrical connectivity to the at least one tissue site.

This overview is intended to provide an overview of the subject matter of the present patent application. It is not intended to provide an exclusive or exhaustive explanation of the invention. The detailed description is included to provide further information about the subject matter of the present patent application.

BRIEF DESCRIPTION OF THE DRAWINGS

In the drawings, which are not necessarily drawn to scale, like numerals describe substantially similar components throughout the several views. Like numerals having different letter suffixes represent different instances of substantially similar components. The drawings illustrate generally, by way of example, but not by way of limitation, various embodiments discussed in the present document.

FIG. 2A illustrates generally an example of a system including an implantable device and more than one terminal for both cardiac and neural stimulation.

FIG. 3 illustrates generally an example of a system including a user confirmation/override.

FIG. 4 illustrates generally an example of a system including an implantable medical device and an external device, the implantable medical device including an electronic energy delivery circuit, an intrinsic electrical signal sensing circuit, a terminal, a validation module, and a notification module.

FIG. 5 illustrates generally an example of a system including an implantable medical device, the implantable medical device including an electrical energy delivery circuit, an intrinsic electrical signal sensing circuit, a terminal, a validation module, and a connectivity module.

DETAILED DESCRIPTION

The following detailed description includes references to the accompanying drawings, which form a part of the detailed description. The drawings show, by way of illustration, specific embodiments in which the invention may be practiced. These embodiments, which are also referred to herein as "examples," are described in enough detail to enable those skilled in the art to practice the invention. The embodiments may be combined, other embodiments may be utilized, or structural, logical and electrical changes may be made without departing from the scope of the present invention. The following detailed description is, therefore, not to be taken in a limiting sense, and the scope of the present invention is defined by the appended claims and their equivalents.

In this document, the terms "a" or "an" are used, as is common in patent documents, to include one or more than one. In this document, the term "or" is used to refer to a nonexclusive or, unless otherwise indicated. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference(s) should be considered supplementary to that of this document; for irreconcilable inconsistencies, the usage in this document controls.

Figure 1:
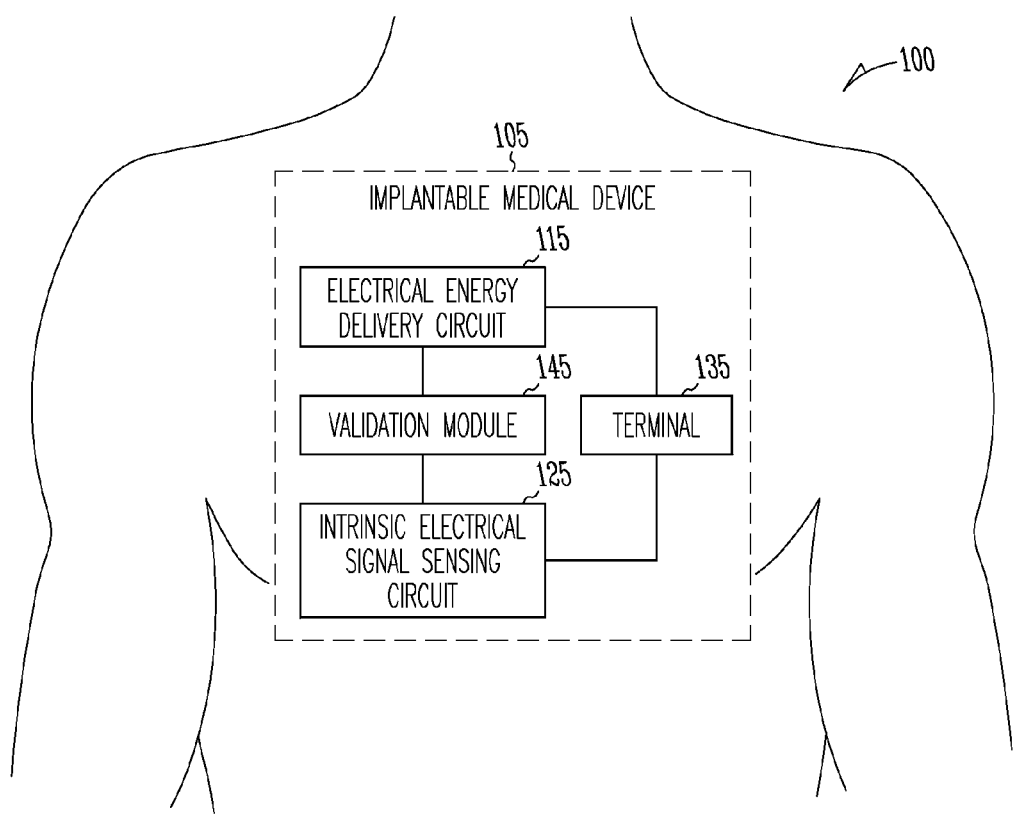
FIG. 1 illustrates generally an example of a system including an implantable medical device, which includes an electrical energy delivery circuit, an intrinsic electrical signal sensing circuit, a terminal, and a validation module.

FIG. 1 is a block diagram illustrating generally an example of portions of a system 100 including an implantable medical device 105, which includes an electrical energy delivery circuit 115, an intrinsic electrical signal sensing circuit 125, a terminal 135, and a validation module 145.

In this example, one or more terminals 135 are configured to couple the electrical energy delivery circuit 115 and the intrinsic electrical signal sensing circuit 125 to at least one tissue site in the body. In other examples, the terminal 135 can include a single terminal, or more than one terminal, to couple one or both of the electrical energy delivery circuit 115 and the intrinsic electrical signal sensing circuit 125 to a single tissue site, or to more than one tissue site, in the body. Thus, a single terminal can connect to an electrode to contact a single tissue site, or to different electrodes respectively located at more than one tissue site, or more than one terminal can connect to a single tissue site or more than one tissue site.

In certain examples, the terminal 135 connects the implantable medical device 105 to at least one tissue site in the body using at least one leadwire or catheter (referred to as a "lead"), where each lead includes one or more electrodes to contact the at least one tissue site. In other examples, the terminal 135 can include any electrical connector between the implantable medical device 105 and an electrical connection to the tissue site.

In the example of FIG. 1, the implantable medical device 105 can include a cardiac stimulator, such as a pacer or cardiac resynchronization therapy (CRT) device to deliver a pacing or resynchronization energy to a cardiac tissue, or a neural stimulator, such as a vagal nerve stimulator (VNS) device to deliver a neurostimulation energy to a non-cardiac neural tissue, or both. In certain examples, the implantable medical device 105 can provide a shocking energy, such as a defibrillation energy. The implantable medical device 105 can include any device configured to deliver an electrical energy to a cardiac tissue, any device configured to deliver an electrical energy to a neural tissue, or any device configured to delivery an electrical energy to a cardiac tissue as well as a neural tissue.

The intrinsic electrical signal sensing circuit 125 is configured to receive an intrinsic electrical signal from a tissue site in the body. An intrinsic electrical signal can also include an electrical characteristic of a tissue site in the body, e.g., the electrical impedance at a tissue site. In certain examples, the intrinsic electrical signal sensing circuit 125 is configured to receive more than one intrinsic electrical signal from one or more tissue sites in the body.

In the example of FIG. 1, the validation module 145 is coupled to the electrical energy delivery circuit 115 and the intrinsic electrical signal sensing circuit 125. In an example, the validation module 145 can be included in the implantable medical device 105. In other examples, the validation module 145 can be an implantable component external to the implantable medical device 105, or can be an external component. The validation module 145 generally determines an indication of a tissue type at the tissue site to which the terminal 135 is coupled. In one example, the validation module 145 receives an intrinsic electrical signal from the intrinsic electrical signal sensing circuit 125 and uses the intrinsic electrical signal to determine the indication of the tissue type at the tissue site. In certain examples, the validation module 145, upon determining the indication of the tissue type at the tissue site, enables or inhibits electrical energy delivery to the tissue site using the determined indication of the tissue type at the tissue site.

Figure 2B:
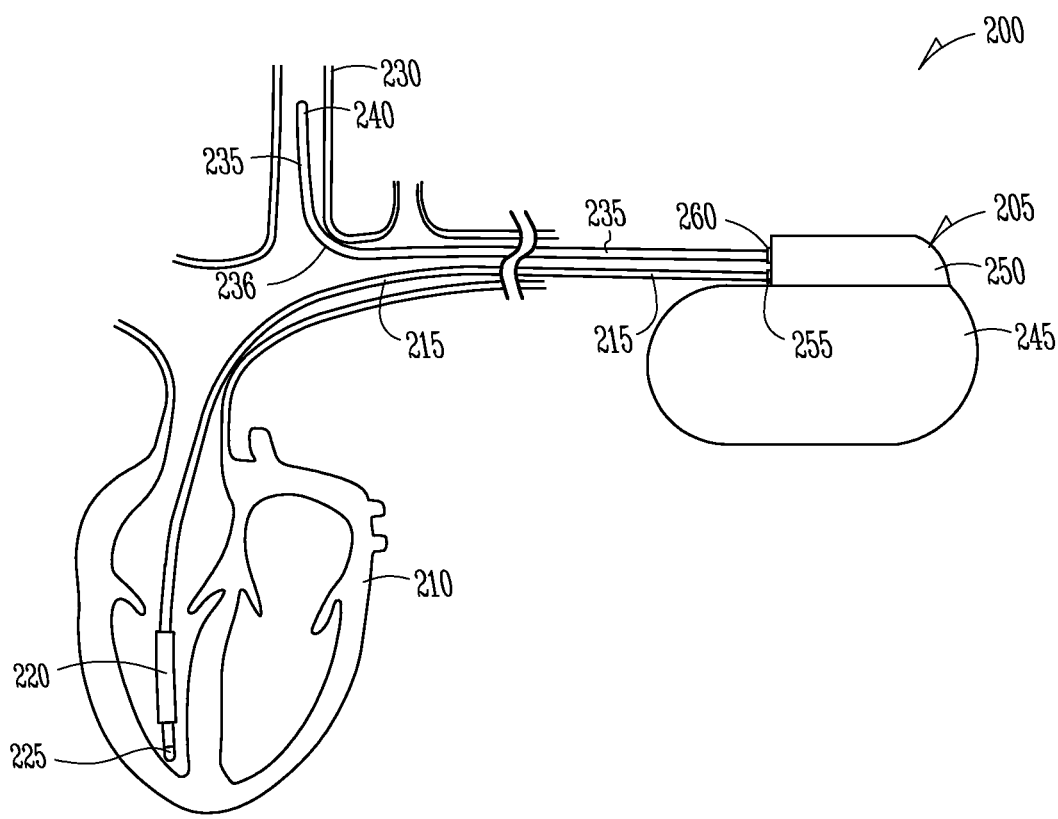
FIG. 2B illustrates generally an example of a system including an implantable device and more than one terminal for both cardiac and neural stimulation.

FIGS. 2A and 2B are block diagrams illustrating generally an example of a system 200 including an implantable medical device 205. In these examples, the implantable medical device 205 can include a header 250 having more than one terminal, e.g., a first terminal 255 and a second terminal 260, such as to permit both cardiac and neural stimulation. Examples of the implantable medical device 205 include any device capable of providing neural or cardiac stimulation.

In certain examples, the implantable medical device 205 includes a hermitically-sealed or similar housing 245 coupled to the header 250. The header 250 can include one or more than one terminal, e.g., the first terminal 255 or the second terminal 260.

In the example of FIGS. 2A and 2B, the system 200 includes a first lead 215 coupled to the first terminal 255. In certain examples, the first lead 215 is configured to provide stimulation to the heart 210 or sense an intrinsic cardiac signal of the heart 210. An intrinsic cardiac signal can include any signal indicative of cardiac activity, e.g., an internal electrocardiogram signal (ECG). In certain examples, the first lead 215 can include a single electrode, e.g., a tip electrode 225, or more than one electrode, e.g., the tip electrode 225 and a ring electrode 220. In other examples, the housing 245 can include an electrode, such as a "case" or a "can" electrode, or the header 250 can include an electrode, such as an indifferent electrode.

In this example, system 200 further includes a second lead 235 coupled to the second terminal 260. In certain examples, the second lead 235 is configured to provide stimulation to a nerve, e.g., the vagal nerve, or to sense an intrinsic neural signal. An intrinsic neural signal can be any signal indicative of neural activity. In other examples, the second lead 235 can include a portion configured to be located in the jugular vein 230 and can include a distal end 240, which can include a nerve stimulation electrode located at or near the distal end 240. In certain examples, the second lead 235 can include a bend 236 associated with the location of the second lead 235, such as in the jugular vein 230. In yet other examples, the second lead 235 can include a cuff electrode, which can be configured to provide stimulation to a nerve or to sense an intrinsic neural signal.

In certain examples, the system 200 includes a single terminal, e.g., the first terminal 255, configured to either provide stimulation to the heart 210 or to sense an intrinsic cardiac signal of the heart 210, or to provide stimulation to a nerve, e.g., the vagal nerve, or to sense an intrinsic neural signal.

FIG. 3 is a block diagram illustrating generally an example of a validation module 145 including a user confirmation/override 146. In certain examples, the validation module 145 can include the user confirmation/override 146, or be coupled to the user confirmation/override 146. In one example, the user confirmation/override 146 is configured to allow a physician, user, or other operator, to either confirm or override the tissue type automatically determined by the validation module 145.

In a certain example, the validation module 145 is configured to automatically determine an indication of a tissue type at the tissue site using the received intrinsic electrical signal, and further, to automatically enable or inhibit electrical energy delivery to the tissue site using the determined indication of the tissue type. In the example of FIG. 3, the user confirmation/override 146 can be configured to require a physician, user, or other operator, to either confirm or override the determination of the validation module 145 before the validation module 145 can enable or inhibit electrical energy delivery to the tissue site. In certain examples, the user confirmation/override 146 is configured to enable or inhibit electrical energy delivery to the tissue site independent of, or in conjunction with, the validation module 145 using physician, user, or other operator input or information.

In certain examples, the user confirmation/override 146 communicates with an external programmer, or other communication device, for operator input. In certain examples, the user confirmation/override 146 is configured to use such operator input only during one or more specific operating modes, e.g., during initial programming after implantation, or during normal operation.

FIG. 4 is a block diagram illustrating generally an example of a system 400 including an implantable medical device 105 and an external device 165. The implantable medical device 105 includes an electrical energy delivery circuit 115, an intrinsic electrical signal sensing circuit 125, a terminal 135, a validation module 145, and a notification module 155. The external device 165 can be implemented using any device capable of communicating with an implantable medical device 105, e.g., an external programmer or remote patient management system such as the LATITUDE system available from the assignee of the present patent application. The external device 165 can incorporate certain functionality that is shown in FIG. 4, for illustrative purposes, as being located in the implantable medical device 105, for example, some or all of the validation module 145 or the notification module 155 could be implemented in the external device 165.

In the example of FIG. 4, the notification module 155 generally notifies a physician, user, or other operator of the determined indication of tissue type, or the determined tissue type, by the validation module 145. In certain examples, the notification module 155 can send to the external device 165 any information received by or sent by the validation module 145, e.g., received intrinsic electrical signals from a tissue site from the intrinsic electrical signal sensing circuit 125, determinations of tissue type from the validation module 145, or "enable" or "inhibit" signals sent to the electrical energy delivery circuit 115.

FIG. 5 is a block diagram illustrating generally an example of a system 500 including an implantable medical device 105. The implantable medical device 105 includes an electrical energy delivery circuit 115, an intrinsic electrical signal sensing circuit 125, a terminal 135, a validation module 145, and a connectivity module 170.

In the example of FIG. 5, the connectivity module 170 is coupled to the intrinsic electrical signal sensing circuit 125 and the electrical energy delivery circuit 115, and generally determines an electrical connectivity (e.g., of the terminal 135) of the implantable medical device 105 to the tissue site. In certain examples, the connectivity module 170 receives an intrinsic electrical signal from the intrinsic electrical signal sensing circuit 125. The connectivity module 170 uses the intrinsic electrical signal to determine the electrical connectivity of the implantable medical device 105 to the tissue site. In certain examples, the connectivity module 170, upon determining the electrical connectivity, then enables or inhibits electrical energy delivery to the tissue site using the determined electrical connectivity. This may include, for example, enabling electrical energy delivery if the lead (e.g., the first lead 215 or the second lead 235) is connected, or inhibiting electrical energy delivery if the lead (e.g., the first lead 215 or the second lead 235) is not connected. This may also include enabling or disabling electrical energy delivery based on the indication of tissue type provided by the validation module 145.

Figure 6:
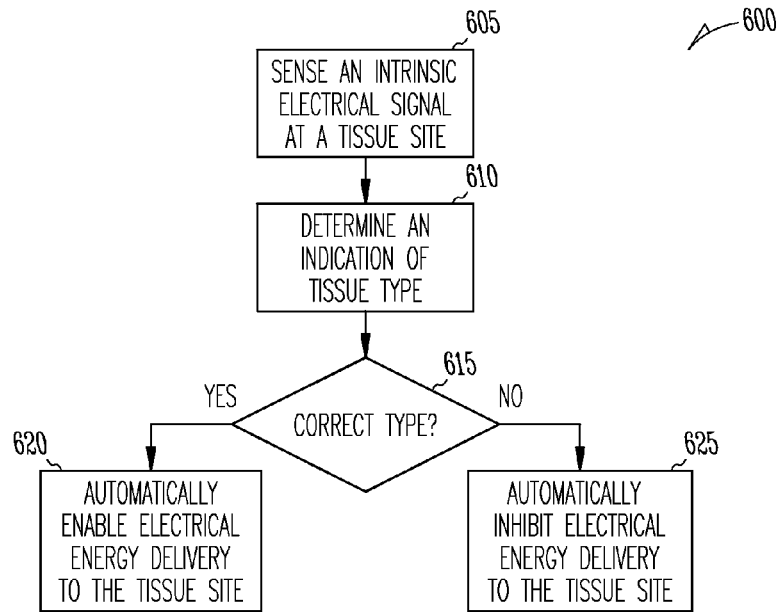
FIG. 6 illustrates generally an example of a method including automatically enabling or inhibiting electrical energy delivery to a tissue site using a determined indication of the tissue type, where the tissue type is determined using a sensed intrinsic electrical signals at the tissue site.

FIG. 6 illustrates generally an example of a method 600 that includes automatically enabling or inhibiting electrical energy delivery to a tissue site by using an indication of the tissue type determined using a sensed intrinsic electrical signal at the tissue site.

In the example of FIG. 6, at 605, an intrinsic electrical signal is sensed at a tissue site. An intrinsic electrical signal can also include an electrical characteristic, e.g., impedance, voltage, etc. In another example, more than one intrinsic electrical signal is sensed at one or more than one tissue site. In one example, the intrinsic electrical signal is sensed using a lead, e.g., the first lead 215 or the second lead 235. In one example, the first lead 215 is configured to sense an intrinsic cardiac signal, and the second lead 235 is configured to sense an intrinsic neural signal. In other examples, one or more than one intrinsic cardiac signal is sensed, or one or more than one intrinsic neural signal is sensed.

At 610, an indication of tissue type at the tissue site is determined. The indication of tissue type can be determined by sensing either cardiac or neural activity in the intrinsic electrical signal sensed at the tissue site. Cardiac activity typically includes activity indicative of a depolarization, repolarization, or cyclical variation of the heart, which usually involves a generally well-defined frequency range, typically varying from 10 Hz to 120 Hz. In contrast, neural activity typically includes activity more akin to "white noise", usually of broader frequency range, and generally including more amplitude or frequency variation.

One or more other distinctive characteristics can be used to distinguish tissue types. One such characteristic is impedance measurement of the tissue at the tissue site. Generally, cardiac tissue can have a different impedance measurement than neural tissue. The desired tissue site may have a known impedance range, e.g., the impedance may be determined upon implantation. In one example, if the impedance measured at the tissue site is not the expected value, the validation module 145 will not enable electrical energy delivery to that tissue site. Another characteristic is signal amplitude at the tissue site. Generally, an intrinsic electrical signal at a cardiac tissue site near the heart will have a high signal amplitude. In contrast, an intrinsic electrical signal at a neural tissue site, e.g., at the vagal nerve in the neck, will typically have a lower signal amplitude. In another example, a cardiac signal can be present at a neural tissue site, e.g., at a neural tissue site near the heart. In these examples, though a cardiac characteristic can be present at the neural site, the indication of tissue type at the tissue site can still be determined to be that of neural tissue.

At 615, if the determined indication of tissue type at the tissue site is determined to be the correct tissue type by the validation module 145, then electrical energy delivery is automatically enabled to the tissue site at 620. In certain examples, the electrical energy delivery circuit 115 is configured to deliver a specific type of energy, e.g., a pacing energy or a neural stimulation energy, to a single or more than one tissue site. In one example, at 615, if, at 610, the determined indication of tissue type is consistent with the type of tissue that the electrical energy delivery circuit 115 was configured to deliver energy to, then validation module 145 is configured to automatically enable electrical energy deliver to the tissue site at 620. At 615, if the determined indication of tissue type at the tissue site is not determined to be the correct tissue type by the validation module 145, then electrical energy delivery is automatically inhibited to the tissue site at 625. In one example, if, at 615, if, at 610, the determined indication of tissue type is not consistent with the type of tissue to which the electrical energy delivery circuit 115 was configured to deliver energy, then validation module 145 is configured to automatically inhibit electrical energy delivery to the tissue site at 625.

In certain examples of FIG. 6, more than one intrinsic electrical signal is being sensed at more than one tissue site. In an example, at 620, electrical energy delivery to the tissue site is enabled in sequence. Sequence enabling can include enabling electrical energy delivery to a first tissue site, e.g., enabling electrical energy delivery to an atrial tissue site upon determining a correct atrial tissue site indication at 615, and then to a second tissue site, e.g., enabling electrical energy delivery to a left ventricle tissue site upon determining a correct left ventricle tissue site indication at 615. Sequence enabling can include any combination of tissue site enabling, e.g., atrial, left ventricular, right ventricular, or neural. In certain examples, one cardiac tissue site can be distinguished from another cardiac tissue site using one or more distinctive characteristics, e.g., impedance, amplitude, etc. In another example, validation module 145 determines if each determined indication of tissue type at each lead, e.g., the first lead 215 or the second lead 235, is the correct tissue type before electrical energy delivery is delivered on any lead, e.g., the first lead 215 or the second lead 235.

Figure 7:
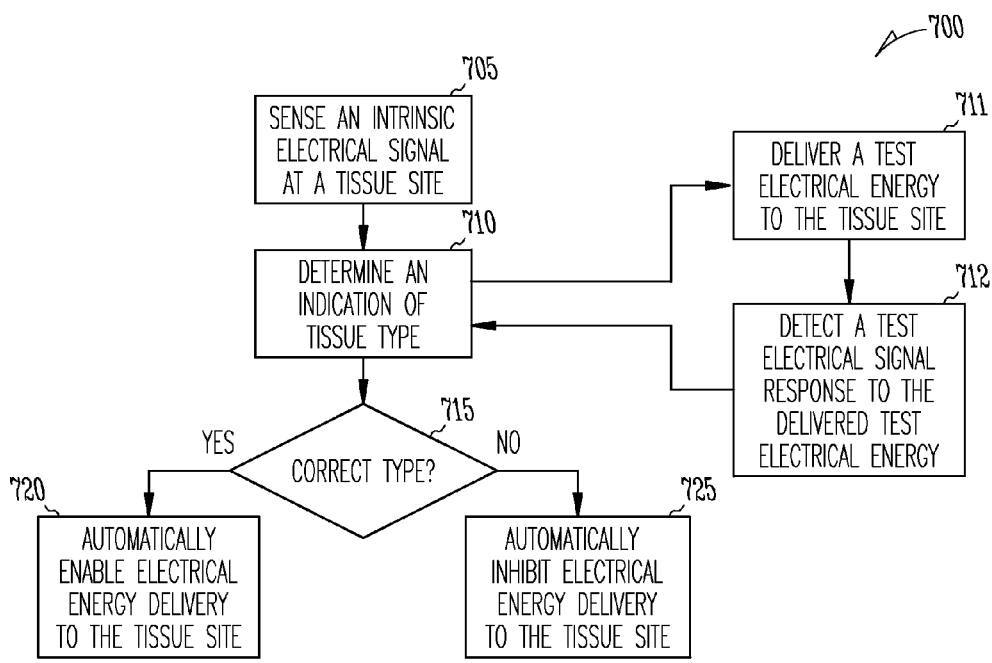
FIG. 7 illustrates generally an example of a method including determining an indication of tissue type, which includes delivering a test electrical energy to the tissue site and detecting a response to the delivered test electrical energy.

FIG. 7 illustrates generally an example of a method 700 including automatically enabling or inhibiting electrical energy delivery to a tissue site using an indication of the tissue type that is determined by delivering a test electrical energy to the tissue site and detecting a response to the delivered test electrical energy.

In the example of FIG. 7, at 705, an intrinsic electrical signal is sensed at a tissue site. At 710, an indication of tissue type at the tissue site is determined. The indication of tissue type can be determined using the intrinsic electrical signal sensed at the tissue site. Alternatively, at 711, a test electrical energy can be delivered to the tissue site. In certain examples, the test electrical energy includes a cardiac stimulation or a neural stimulation. The cardiac stimulation or neural stimulation can include a stimulation designed to be strong enough to cause a stimulation response, but weak enough to not harm the tissue the stimulation is being delivered to. The response to the test electrical energy can be indicative of the tissue type at the tissue site, e.g., a cardiac contraction. The test electrical energy delivery at 711 is typically of a short duration, configured to either detect a response or the lack of a response. At 712, a test electrical signal response to the delivered test electrical energy is detected. Thus, at 710, an indication of tissue type at the tissue site can be determined using the detected test electrical signal response at 712 to the delivered test electrical energy at 711.

In an example, at 711, a test electrical energy is delivered to the tissue site, such that the test electrical energy is safe for neural tissue and sufficient to cause a cardiac response. In certain examples, a test electrical energy of a low amplitude, low frequency, or small pulse-width is safe for neural tissue and sufficient to cause a cardiac response. In one example, a test electrical energy of low amplitude, low frequency, or small pulse-width that is safe for neural tissue and sufficient to cause a cardiac response includes a single 4 Volt pulse to a tissue site having an impedance of 1 k Ohms, which delivers roughly 4 mA of current to the tissue site. In other examples, more than one pulse can be delivered with a low repetition rate or small pulse width and can be safe for neural tissue and sufficient to cause a cardiac response. At 712, delivery of the test electrical energy ceases to avoid damage to the tissue site.

At 715, if the determined indication of tissue type at the tissue site is determined to be the correct tissue type by the validation module 145, then electrical energy delivery is automatically enabled to the tissue site at 720. At 715, if the determined indication of tissue type at the tissue site is not determined to be the correct tissue type by the validation module 145, then electrical energy delivery is automatically inhibited to the tissue site at 725.

Figure 8:
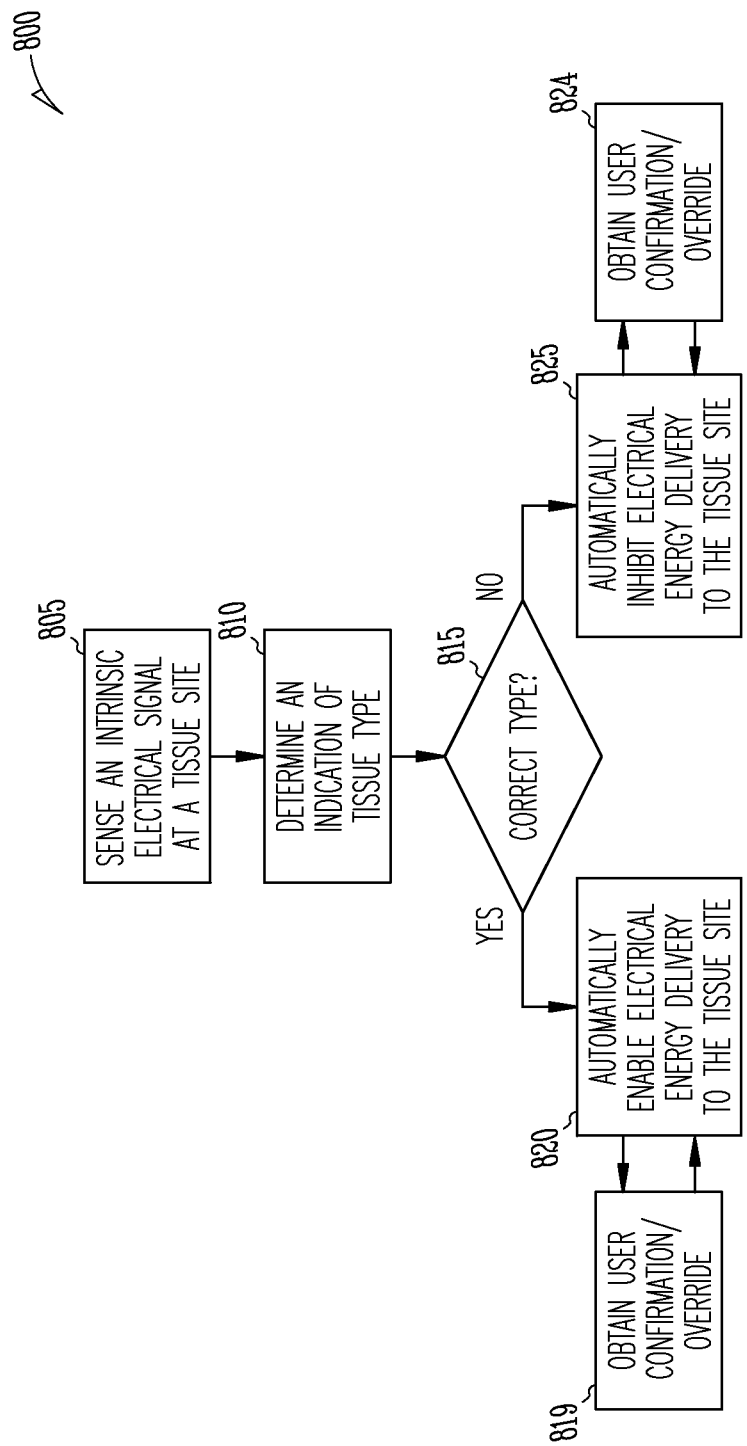
FIG. 8 illustrates generally an example of a method including obtaining a user confirmation/override.

FIG. 8 illustrates generally an example of a method 800 including automatically enabling or inhibiting electrical energy delivery to a tissue site using a automatically determined indication of the tissue type, including obtaining a user confirmation/override.

In the example of FIG. 8, at 805, an intrinsic electrical signal is sensed at a tissue site. At 810, an indication of tissue type at the tissue site is automatically determined, such as by using the intrinsic electrical signal sensed at the tissue site, or by delivering a test electrical energy and using a test electrical energy response.

At 815, if the determined indication of tissue type at the tissue site is determined to be the correct tissue type by the validation module 145, then electrical energy delivery is automatically enabled to the tissue site at 820. At 815, if the determined indication of tissue type at the tissue site is not determined to be the correct tissue type by the validation module 145, then electrical energy delivery is automatically inhibited to the tissue site at 825.

However, at 819 and 824, before the validation module 145 automatically enables or inhibits electrical energy delivery to the tissue site at 820 or 825, a user confirmation/override 146 can be required. This would require either confirmation or override, by a physician, user, or other operator, of the determination of the validation module 145 to automatically enable or inhibit electrical energy delivery to the tissue site.

Figure 9:
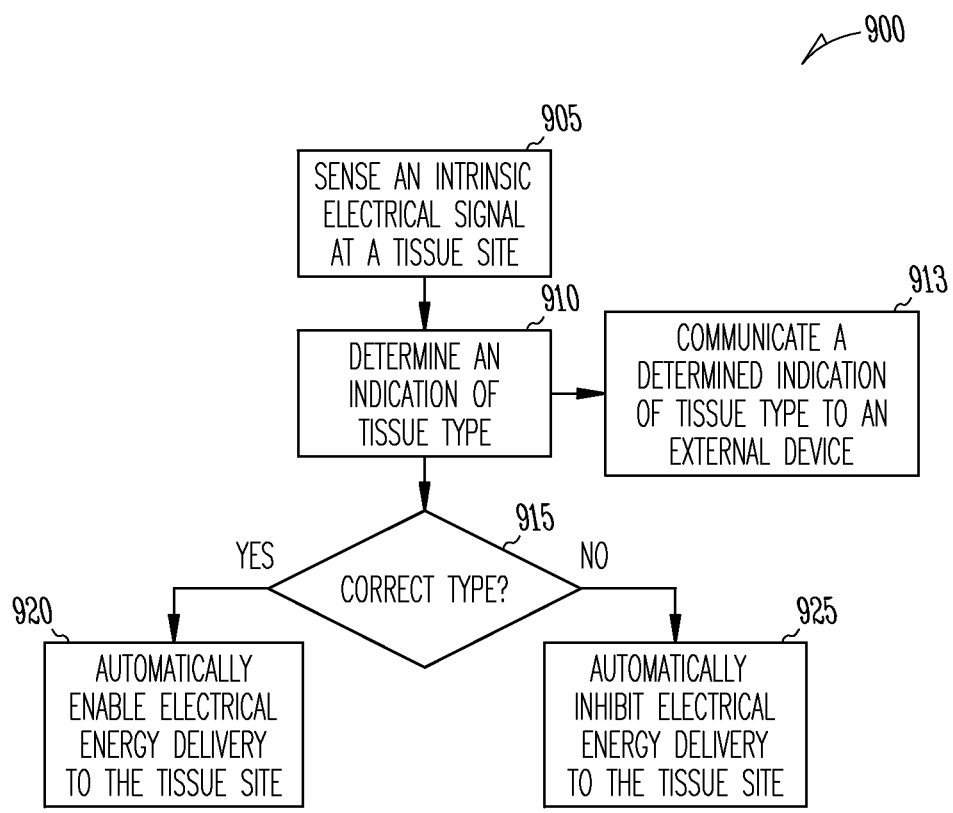
FIG. 9 illustrates generally an example of a method including communicating an indication of tissue type to an external device.

FIG. 9 illustrates generally an example of a method 900 including automatically enabling or inhibiting electrical energy delivery to a tissue site using an automatically determined indication of the tissue type, including communicating an indication of tissue type to an external device.

In the example of FIG. 9, at 905, an intrinsic electrical signal is sensed at a tissue site. At 910, an indication of tissue type at the tissue site is determined. The indication of tissue type can be determined using the intrinsic electrical signal sensed at the tissue site. Alternatively, the indication of tissue type can be determined using a test electrical energy and a test electrical energy response.

At 913, a notification module 155 communicates the determined indication of tissue type, from 910, to an external device 165. The external device can include a medical device programmer, a user display, or any other device capable of displaying, to a physician, user, or other operator, or storing the determined indication of tissue type.

At 915, if the determined indication of tissue type at the tissue site is determined to be the correct tissue type by the validation module 145, then electrical energy delivery is automatically enabled to the tissue site at 920. At 915, if the determined indication of tissue type at the tissue site is not determined to be the correct tissue type by the validation module 145, then electrical energy delivery is automatically inhibited to the tissue site at 925.

Figure 10:
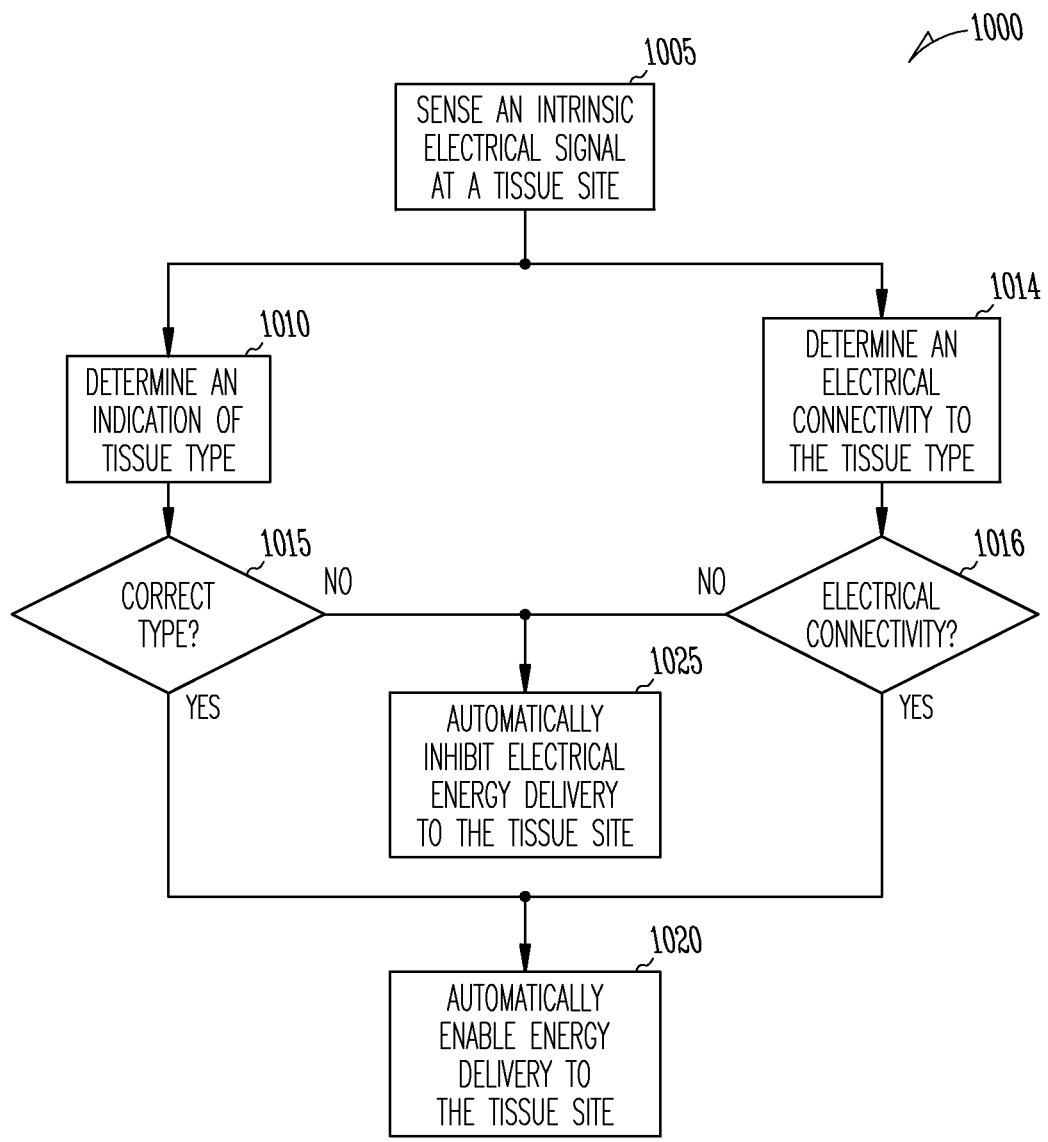
FIG. 10 illustrates generally an example of a method including automatically enabling or inhibiting electrical energy delivery to a tissue site using a determined electrical connectivity to the tissue type, where the connectivity is determined using a sensed intrinsic electrical signals at the tissue site.

FIG. 10 illustrates generally an example of a method 1000 including automatically enabling or inhibiting electrical energy delivery to a tissue site using a determined electrical connectivity to the tissue type, where the connectivity is determined using a sensed intrinsic electrical signals at the tissue site.

In the example of FIG. 10, at 1005, an intrinsic electrical signal is sensed at a tissue site. At 1010, an indication of tissue type at the tissue site is determined. The indication of tissue type can be determined using the intrinsic electrical signal sensed at the tissue site. Alternatively, the indication of tissue type can be determined using a test electrical energy and a test electrical energy response.

At 1015, if the determined indication of tissue type at the tissue site is determined to be the correct tissue type by the validation module 145, then electrical energy delivery can be automatically enabled to the tissue site at 1020. At 1015, if the determined indication of tissue type at the tissue site is not determined to be the correct tissue type by the validation module 145, then electrical energy delivery can be automatically inhibited to the tissue site at 1025.

At 1014, an electrical connectivity to the tissue site is determined. The electrical connectivity to the tissue site can be determined by using the sensed intrinsic electrical signal at the tissue site. In one example, an impedance measurement is taken at the tissue site. If a substantially high impedance is measured, e.g., much higher than a normal tissue impedance, then the terminal 135 may not be coupled to the tissue site.

At 1016, if the terminal 135 is determined to be electrically connected to the tissue site by the connectivity module 170, then electrical energy delivery can be automatically enabled to the tissue site at 1020. At 1016, if the terminal 135 is determined to not be electrically connected to the tissue site by the connectivity module 170, then electrical energy delivery can be automatically inhibited to the tissue site at 1025.

In one example, at 1020, electrical energy delivery to the tissue site can be automatically enabled if either the determined indication of tissue type at the tissue site is determined to be the correct tissue type by the validation module 145, at 1015, or the terminal 135 is determined to be electrically connected to the tissue site by the connectivity module 170, at 1016. In another example, at 1020, electrical energy delivery to the tissue site can be automatically enabled if both the determined indication of tissue type at the tissue site is determined to be the correct tissue type by the validation module 145, at 1015, and the terminal 135 is determined to be electrically connected to the tissue site by the connectivity module 170, at 1016.

In one example, at 1025, electrical energy delivery to the tissue site can be automatically inhibited if either the determined indication of tissue type at the tissue site is not determined to be the correct tissue type by the validation module 145, at 1015, or the terminal 135 is determined to not be electrically connected to the tissue site by the connectivity module 170, at 1016. In another example, at 1025, electrical energy delivery to the tissue site can be automatically inhibited if both the determined indication of tissue type at the tissue site is not determined to be the correct tissue type by the validation module 145, at 1015, and the terminal 135 is determined to not be electrically connected to the tissue site by the connectivity module 170, at 1016.

Figure 11:
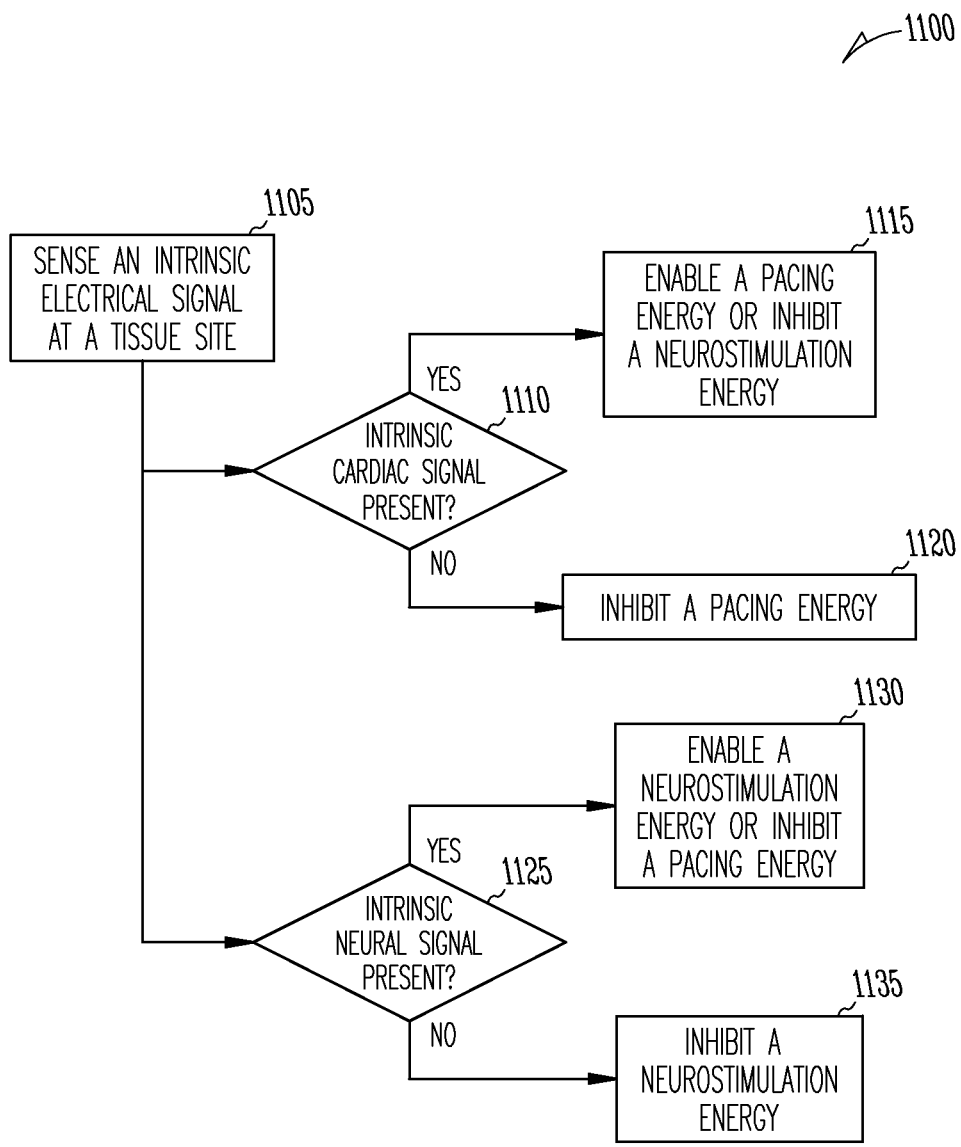
FIG. 11 illustrates generally an example of a method including enabling a pacing energy and inhibiting a neurostimulation energy if an intrinsic cardiac signal is present, inhibiting a pacing energy if an intrinsic cardiac signal is not present, enabling a neurostimulation energy and inhibiting a pacing energy if an intrinsic neural signal is present, and inhibiting a neurostimulation energy if an intrinsic neural signal is not present.

FIG. 11 illustrates generally an example of a method 1100 including enabling a pacing energy or inhibiting a neurostimulation energy if an intrinsic cardiac signal is present, inhibiting a pacing energy if an intrinsic cardiac signal is not present, enabling a neurostimulation energy or inhibiting a pacing energy if an intrinsic neural signal is present, and inhibiting a neurostimulation energy if an intrinsic neural signal is not present.

In the example of FIG. 11, at 1105, an intrinsic electrical signal is sensed at a tissue site. At 1110, if the intrinsic electrical signal sensed at 1105 includes an intrinsic cardiac signal, then a pacing energy is enabled or a neurostimulation energy is inhibited at 1115. Alternatively, any cardiac stimulation can be enabled, or any neural stimulation can be inhibited at 1115. At 1110, if the intrinsic electrical signal sensed at 1105 does not include an intrinsic cardiac signal, then a pacing energy is inhibited at 1120. Alternatively, any cardiac signal can be inhibited at 1120.

At 1125, if the intrinsic electrical signal sensed at 1105 includes an intrinsic neural signal, then a neurostimulation energy is enabled or a pacing energy is inhibited at 1130. Alternatively, any neural stimulation can be enabled, or any cardiac stimulation can be inhibited at 1130. At 1125, if the intrinsic electrical signal sensed at 1105 does not include an intrinsic neural signal, then a neuro stimulation energy is inhibited at 1135. Alternatively, any neural stimulation can be inhibited at 1135.

In the examples of FIGS. 6-11, various examples, including sensing an intrinsic electrical signal at a tissue site, determining an indication of tissue type at the tissue site, or automatically enabling or inhibiting electrical energy delivery to the tissue site, are disclosed. It is to be understood that these examples are not exclusive, and can be implemented either alone or in combination, or in various permutations or combinations.

It is to be understood that the above description is intended to be illustrative, and not restrictive. For example, the above-described embodiments (and/or aspects thereof) may be used in combination with each other. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain-English equivalents of the respective terms "comprising" and "wherein." Also, in the following claims, the terms "including" and "comprising" are open-ended, that is, a system, device, article, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

The Abstract is provided to comply with 37 C.F.R. §1.72 (b), which requires that it allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description, with each claim standing on its own as a separate embodiment.

What is claimed is:

1. A method comprising:
sensing a characteristic at at least one tissue site;
determining, using a validation module of a medical device, an indication of a cardiac tissue type or a neural tissue type at the at least one tissue site using the sensed characteristic; and
in response to determining the indication of the tissue type indicates cardiac tissue, enabling cardiac pacing electrical energy delivery and inhibiting neurostimulation electrical energy delivery to the at least one tissue site and
in response to the determining the indication of the tissue type indicates neural tissue, enabling neurostimulation electrical energy delivery and inhibiting cardiac pacing electrical energy delivery to the at least one tissue site.

2. The method of claim 1, wherein the sensing the characteristic comprises sensing an intrinsic cardiac signal, and wherein the determining the indication of a tissue type includes using a characteristic of the intrinsic cardiac signal.

3. The method of claim 1, wherein the sensing the characteristic comprises sensing an intrinsic neural signal, and wherein the determining the indication of a tissue type includes using a characteristic of the intrinsic neural signal.

4. The method of claim 1, wherein the sensing the characteristic includes using at least one electrode to sense at least one intrinsic cardiac signal and at least one electrode to sense at least one intrinsic neural signal, wherein the multiple electrodes are coupled to a single lead.

5. The method of claim 1, wherein the enabling energy delivery includes enabling energy delivery at multiple tissue sites.

6. The method of claim 1, wherein the inhibiting energy delivery includes inhibiting energy delivery at multiple tissue sites.

7. The method of claim 1, further comprising receiving an operator confirmation or override before the enabling or inhibiting.

8. The method of claim 1, further comprising delivering a pacing electrical energy to the cardiac tissue in response to the enabling cardiac pacing electrical energy delivery to the at least one tissue site.

9. The method of claim 1, further comprising delivering a neurostimulation energy to the neural tissue in response to the enabling the neurostimulation electrical energy delivery to the at least one tissue site.

10. The method of claim 1, wherein the determining the indication of a tissue type using the sensed characteristic comprises:
delivering a test electrical energy to the at least one tissue site; and
detecting a test electrical response signal to the delivering of the test electrical energy to the at east one tissue site.

11. The method of claim 10, wherein the delivering the test electrical energy includes delivering a cardiac pacing energy.

12. The method of claim 10, wherein the delivering the test electrical energy includes delivering a neurostimulation energy.

13. The method of claim 1, wherein at least one of the enabling energy delivery or the inhibiting energy delivery is performed automatically without user intervention.

14. The method of claim 1, wherein the sensing the characteristic comprises sensing at least one intrinsic electrical signal.

15. The method of claim 1, comprising communicating to an external device information about the determined indication of the tissue type.

16. The method of claim 1, comprising:
determining an electrical connectivity to the at least one tissue site and
automatically enabling electrical energy delivery to the at least one tissue site using the determined electrical connectivity to the at least one tissue site.

17. The method of claim 1, comprising:
determining an electrical connectivity to the at least one tissue site; and
automatically inhibiting electrical energy delivery to the at least one tissue site using the determined electrical connectivity to the at least one tissue site.

18. A method comprising:
sensing an electrical characteristic at at least one tissue site;
determining, using a validation module of a medical device, at least one indication of a tissue type at the at least one tissue site using the sensed electrical characteristic;
receiving a user confirmation or override of the determined at least one indication of the tissue type at the at least one tissue site; and
in response to determining the indication of the tissue type indicates cardiac tissue, enabling cardiac pacing electrical energy delivery and inhibiting neurostimulation electrical energy delivery to the at least one tissue site; and
in response to determining the indication of the tissue type indicates neural tissue, enabling neurostimulation electrical energy delivery and inhibiting cardiac pacing electrical energy delivery to the at least one tissue site.

19. The method of claim 18, wherein the sensing the electrical characteristic comprises sensing at least one of an intrinsic cardiac signal or an intrinsic neural signal, and wherein the determining at least one indication of a tissue type comprises using the sensed intrinsic cardiac signal or the sensed intrinsic neural signal to determine the at least one indication of the tissue type.

20. A method comprising:

sensing a characteristic at at least one tissue site;

determining, using a validation module of a medical device, at least one indication of a tissue type at the at least one tissue site using the sensed characteristic;

obtaining, using an input device communicatively coupled to the validation module, a user confirmation or override of the determined at least one indication of a tissue type;

communicating the user confirmation or override from the input device to the validation module; and in response to determining the indication of the tissue type indicates cardiac tissue, (1) enabling cardiac pacing electrical energy delivery and delivering a pacing electrical energy to the cardiac tissue, and (2) inhibiting neurostimulation electrical energy delivery to the at least one tissue site; and in response to determining the indication of the tissue type indicates neural tissue, (1) enabling neurostimulation electrical energy delivery and delivering a neurostimulating electrical energy to the neural tissue and (2) inhibiting cardiac pacing electrical energy delivery to the at least one tissue site.

\* \* \* \* \*